United States Patent [19]

Stivala

[11] 4,224,941

[45] Sep. 30, 1980

[54] HYPERBARIC TREATMENT APPARATUS

[76] Inventor: Oscar G. Stivala, 10 Whited St., Little Falls, N.Y. 13365

[21] Appl. No.: 960,962

[22] Filed: Nov. 15, 1978

[51] Int. Cl.³ ............................................ A61M 35/00
[52] U.S. Cl. ................................................ 128/207.26
[58] Field of Search ............... 128/184, 172, 204, 205, 128/191 A, 39, 40, 30.2, 299, 298, 300, 202, 132 R, 185, 207.26

[56] References Cited

U.S. PATENT DOCUMENTS

| | | | |
|---|---|---|---|
| 2,742,900 | 4/1956 | Giorgio et al. | 128/205 |
| 3,045,672 | 7/1962 | Croasdaile | 128/205 |
| 3,357,426 | 12/1967 | Cohen | 128/205 |
| 3,786,809 | 1/1974 | Kitrilakis | 128/191 A |
| 3,824,998 | 7/1974 | Snyder | 128/132 R |

Primary Examiner—Henry J. Recla
Attorney, Agent, or Firm—Bruns & Jenney

[57] ABSTRACT

An inexpensive disposable hyperbaric treatment device that can be conveniently applied to any part of the body to treat skin disorders such as ulcers or the like. The device consists of a pliable adhesive backed pad having a central opening formed therein for framing the treatment region and a flaccid bag secured to the top surface of the pad that is adapted to receive a treatment gas under pressure. A collar is provided about the rim of the opening inside the bag so that the pressured gas acts against the pad to insure proper sealing at the opening.

11 Claims, 3 Drawing Figures

HYPERBARIC TREATMENT APPARATUS

BACKGROUND OF THE INVENTION

This invention relates to a hyperbaric treatment device and, in particular, to a hyperbaric device that can be easily applied to any part of the body for treating skin disorders.

The most pertinent prior art known to the applicant at the time of filing this case can be found in the following U.S. patents:
U.S. Pat. No. 3,450,450
U.S. Pat. No. 3,610,238
U.S. Pat. No. 3,712,298
U.S. Pat. No. 3,744,491
U.S. Pat. No. 4,003,371

It has been known for quite some time that many types of skin disorders, such as ulcers, burns, venous stasis, sores and the like, can be effectively treated by applying hyperbaric oxygen to the afflicted region. The pressurized treatment gas has been found to suppress bacterial growth, promote tissue granulation and accelerate epithelization. However, as evidenced by the disclosures in the above noted patents, most of the prior art devices involve rather complex and cumbersome machines that are specifically designed to treat only the body extremities. In practice, the entire limb is typically inserted into an opening provided within a chamber and the opening made gastight by placing a tourniquette-like seal about the limb. With the seal in place, pressurized gas is introduced into the chamber.

Many of the prior art machines are only available on a very limited basis because of the costs involved in building and maintaining this type of complex equipment. Generally these machines are found only at special locations, such as hospitals, having a specially trained staff that is qualified to run the device. The use of tourniquette-like seals has also been found to be objectional in that they pose a potential hazard to the general circulation of the patient. The reusable machine also requires a thorough cleaning between treatments which requires considerable down time and thus further limits the effective utilization of the equipment.

SUMMARY OF THE INVENTION

It is therefore an object of the present invention to improve hyperbaric devices used in treating various forms of skin disorders.

A further object of the present invention is to promote wider use of hyperbaric gas for the treatment of skin ailments by providing an inexpensive and easy to use treatment apparatus.

Another object of the present invention is to provide hyperbaric treatment apparatus that can be operatively applied to any part of the body without impeding the general circulation of the user.

Yet another object of the present invention is to provide an inexpensive hyperbaric treatment device that can be conveniently thrown away after each treatment.

These and other objects of the present invention are attained by means of a hyperbaric device containing a pliable base pad having a central opening formed therein and having an adhesive coating on the outer surface thereof, a flaccid bag secured to the top surface of the pad by means of a collar which surrounds the opening whereby a hyperbaric treatment chamber is formed over the opening, and means to provide a flow of hyperbaric treatment gas into and out of the bag whereby the gas exerts a sealing pressure against the collar while at the same time it is utilized to treat the afflicted skin area.

BRIEF DESCRIPTION OF THE DRAWINGS

For a better understanding of these and other objects of the present invention, reference is had to the following detailed description of the invention which is to be read in conjunction with the following drawings, wherein.

DESCRIPTION OF THE INVENTION

Oxygen under pressure has been used to treat skin ulcers and other types of skin disorders for quite some time. Applying dry oxygen under a pressure of between 5 and 25 mm of Hg. produces an antiseptic action, stimulates granulation of the tissue and promotes ephithelial formation which all contributes to rapid healing. To avoid interference with capillary circulation, the operating pressure should not exceed 25 mm Hg. for any appreciable period of time. Oxygen applied to the treatment region under ambient pressures, on the other hand, has little or no effect on the healing process.

The present invention, as presented in the accompanying drawings, represents a safe, simple and inexpensive means for administering hyperbaric oxygen, or any other suitable treatment gas, to the skin of a patient. As will become evident, the device is not limited in its application to the treatment of body extremities but can be applied to any afflicted region of the body without having to resort to the use of large bulky chambers or other similarly complicated pieces of equipment.

Figure 1:
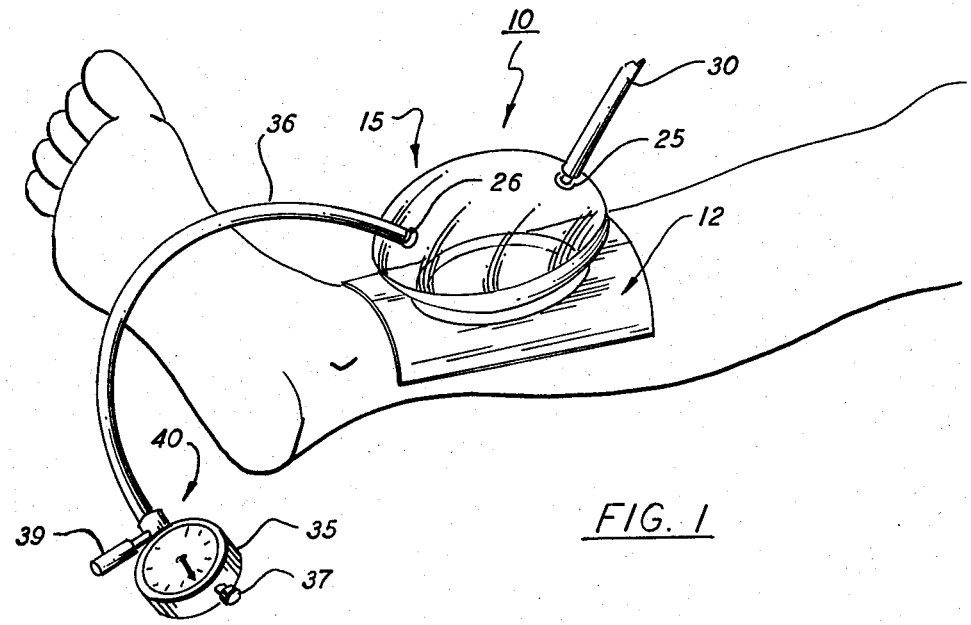
FIG. 1 is a perspective view of a hyperbaric device embodying the teachings of the present invention showing the bag operatively positioned upon the leg of a patient.
Figure 2:
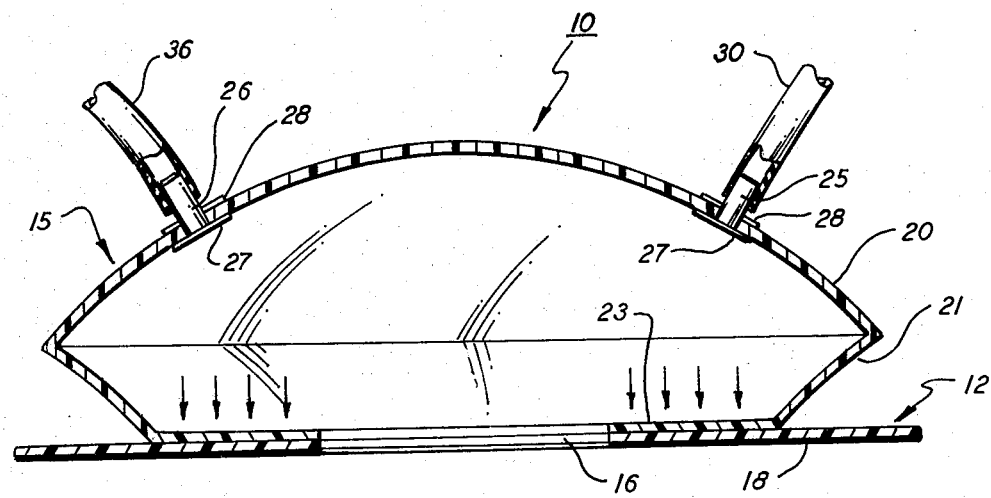
FIG. 2 is an enlarged side elevation in section further illustrating the hyperbaric device shown in FIG. 1 wherein the treatment chamber in an inflated condition.

As shown best in FIGS. 1 and 2, the hyperbaric treatment device 10 of the present invention includes a pliable base pad 12 to which is securely affixed an inflatable bag 15. The pad is provided with a centrally located opening 16 formed therein. In practice, the pad is placed over the afflicted skin region with the opening framing the area to be treated. The outer surface of the pad, that is, the surface opposite that to which the bag is affixed, has an adhesive coating 18 applied thereto which enables the device to be attached to the skin of the patient. Although not shown, the adhesive layer is normally protected by a tear-away strip which is removed just prior to usage.

Experiments have shown that many known and commercially available adhesives can be operatively linked or bonded to plastic materials to provide an extremely strong adhering surface capable of forming a gastight bond when applied to human skin. Tests conducted on simple plastic colostomy bags using this type of adhesive coating have demonstrated that the bag can withstand internal gas pressures in excess of 25 mm Hg. without the bag leaking or becoming detached from the skin. Accordingly, this type of adhesive bonding material can be used in the present system to provide a strong and reliable seal capable of resisting the recommended gas pressures.

Referring more specifically to FIG. 2, the flaccid bag includes an arcuate shaped roof 20 that is provided with one or more depending side panels 21 that acts as a pleat to allow the roof of the bag to be collapsed downwardly against the pad. The panel, in turn, is secured to an annular collar 23 which surrounds the opening contained in the base pad and forms a sealing ring about the opening.

In practice, the roof, side panel and collar are preferably formed from a single piece of pliable transparent plastic material using well known fabrication techniques. The base pad can also be formed of the same material. In final assembly, the collar is bonded to the pad to create an inflatable treatment chamber about the opening. Bonding of the collar to the pad can be achieved using well known thermal techniques.

A pair of female hose connectors 25,26 are mounted within the roof of the flaccid bag by use of thermally bonded gromets 27,28 or any other suitable means. Connector 25, which herein serves as an inlet port to the bag is connected to a source of humidified oxygen (not shown) via supply hose 30. The other connector 26 serves as an outlet port and is similarly connected to a flow control regulator 35 by means of outlet hose 36.

The flow regulator may be of any suitable construction or design. A monometer, as typically used in conjunction with many types of blood pressure measuring instruments, may be conveniently utilized in the system. A control valve 37 is operatively associated with the monometer. The valve can be set to allow passage of a determinable amount of treatment gas through the system. A safety valve 39 is also located at the connector 40 to the flow regulator which will open automatically when the pressure within the system exceeds desirable limits. In most cases the safety valve will be set to open at a pressure of about 25 mm Hg.

Initially, the pad is adhered to the skin about the treatment area with the afflicted region about centered within the opening, and a supply of treatment gas is connected to the inlet port. The regulator is similarly connected to the exhaust port and the pressure and flow rate of gas through the system set to a desired level. This, in turn, causes the bag to become inflated whereupon the afflicted skin area is exposed to a quantity of gas under pressure. The pressurized gas within the bag also exerts a force on the back side of the collar (as indicated by the arrows in FIG. 2) to create a sealing pressure about the entire perimeter of the opening. This sealing pressure acts generally normal to the top surface of the collar. By maintaining the surface area of the collar relatively large in respect to the combined height of the pad and the collar within the opening, the sealing forces acting on the collar will be substantially greater than the lifting forces acting under the pad which tend to tear the pad from the skin at the opening. This, combined with the adhesive holding power of the pad, prevents the bag from leaking when inflated to the desired operating pressure. By maintaining the surface area of the collar at about equal to one quarter the total surface area of the pad, the entire system can be adequately sealed against leakage.

Figure 3:
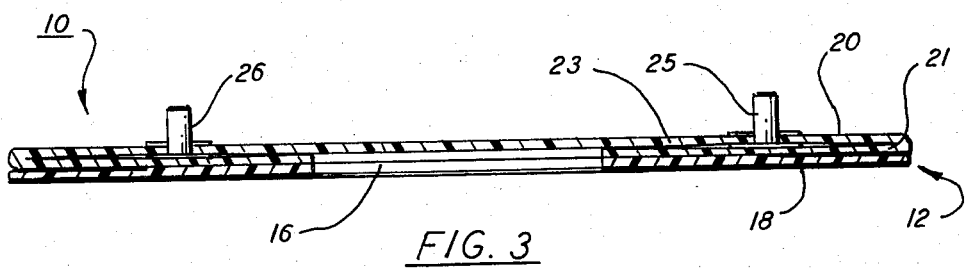
FIG. 3 is also a side elevation in section of the hyperbaric device shown in FIG. 2 showing the chamber in a collapsed condition.

As illustrated in FIG. 3, the bag can be collapsed by simply folding the side panel or panels down against the pad. With the supply and exhaust hoses removed from the bag, a relatively thin, low profile, structure is formed which lends itself to packaging, shipping and storage. Because the bag and pad assembly can be manufactured from lightweight relatively inexpensive plastic materials, it is envisioned that the pad and bag assembly will be utilized for a single treatment and then disposed of. This, of course, eliminates a considerable amount of upkeep and maintenance time and provides for a cleaner and more sanitary procedure.

It should be clear that the size and the shape of the present device is not limited to the particular embodiment as shown in the drawings and the invention is not necessarily confined to the specific details as herein set forth. This application is, in fact, intended to cover any modification that may come within the scope of the following claims.

I claim:

1. Apparatus for administering hyperbaric treatment gas to a region of the skin including
    a pliable pad having a centrally located opening formed therein for framing the skin treatment region, the pad having an adhesive coating on the outer surface thereof whereby it may be securely attached to the surface of the skin adjacent the treatment region,
    a pliable annular collar bonded to the inner surface of the pad with the collar completely surrounding the opening formed in said pad,
    a gastight bag bonded to the outer periphery of said collar to provide a hyperbaric treatment chamber over said opening and also over the collar, and
    a gas inlet port and a gas outlet port operatively connected to the bag whereby a supply of treatment gas under pressure may be transported into and out of the treatment chamber for providing treatment to the skin and for applying a sealing pressure against the collar.

2. The apparatus of claim 1 in which the bag is formed of a flaccid transparent plastic material whereby the treatment region may be viewed through said bag.

3. The apparatus of claim 1 wherein the surface area of the collar is equal to about one-fourth of the total surface area of the pad.

4. The apparatus of claim 1 wherein the bag includes a roof section that is connected to the collar by means of at least one collapsible side panel whereby the roof section may be folded downwardly against the pliable pad.

5. The apparatus of claim 1 wherein said inlet and outlet ports connected to the bag are male hose connectors that are adaptable to slidably receive treatment gas hoses in gastight relationship therewith.

6. Apparatus for administering hyperbaric treatment gas to a region of the skin including
    a pliable pad having a centrally positioned opening therein for framing the skin treatment region and having an adhesive coating on the outer surface thereof whereby the pad can be securely attached to the skin adjacent to the treatment region,
    an airtight flaccid bag that is secured to the inner surface of said pad about said opening at the predetermined distance from the periphery of the opening so that a collar is formed about the opening inside the bag,
    means to bring a treatment gas under pressure into said bag to inflate said bag whereby the treatment gas is caused to act downwardly against the collar to form a pressure seal around the opening, and flow regulator means operatively connected to the bag for maintaining the pressure within the bag at a predetermined level.

7. The apparatus of claim 6 wherein said flow regulator means includes a monometer.

8. The apparatus of claim 6 wherein the surface area of the collar is about one fourth the total surface area of the pad.

9. The apparatus of claim 6 wherein the flaccid bag is formed of a transparent plastic material to permit the skin treatment region to be visually observed therethrough.

10. The apparatus of claim 7 further including a control valve for regulating the amount of gas passing through the system.

11. The apparatus of claim 6 which further includes a safety valve operatively connected to the regulating means for relieving the pressure within the bag when said pressure exceeds a prescribed limit.

* * * * *